US009615427B1

(12) United States Patent
Narayanan et al.

(10) Patent No.: US 9,615,427 B1
(45) Date of Patent: Apr. 4, 2017

(54) EXPLOITING CONSTRUCTIVE INTERFERENCE FROM AMBIENT CONDITIONS

(71) Applicant: TEXAS INSTRUMENTS INCORPORATED, Dallas, TX (US)

(72) Inventors: Sriram Narayanan, Richardson, TX (US); Srinath Ramaswamy, Murphy, TX (US); Arup Polley, Richardson, TX (US); Ajit Sharma, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/954,618

(22) Filed: Nov. 30, 2015

(51) Int. Cl.
*H05B 37/02* (2006.01)
*A61B 5/00* (2006.01)
*H05B 33/08* (2006.01)
*A61B 5/024* (2006.01)
*A61B 5/1455* (2006.01)

(52) U.S. Cl.
CPC ..... *H05B 37/0218* (2013.01); *A61B 5/02416* (2013.01); *A61B 5/14551* (2013.01); *H05B 33/0854* (2013.01); *H05B 37/0281* (2013.01)

(58) Field of Classification Search
CPC H05B 37/02; H05B 37/0218; H05B 37/0281; H05B 33/08; H05B 33/0854; A61B 5/02416; A61B 5/14551

USPC .......... 315/150–156, 291, 307, 308; 600/301
See application file for complete search history.

(56) References Cited

U.S. PATENT DOCUMENTS

2013/0096392 A1\* 4/2013 Adams ................ A61B 5/0075
600/301

\* cited by examiner

*Primary Examiner* — Jimmy Vu
(74) *Attorney, Agent, or Firm* — John R. Pessetto; Charles A. Brill; Frank D. Cimino

(57) ABSTRACT

An optical system includes an optical illumination source, an optical receiver, a correlation determination circuit, and an ambient condition control circuit. The optical illumination source is configured to emit a light in the direction of a target object. The optical receiver is configured to receive a combined optical signal that includes an ambient light component combined with an interrogation component. The correlation determination circuit is configured to compare the combined optical signal with an ambient light signal to identify a correlation factor. The ambient condition control circuit is configured to compare the correlation factor to a low correlation threshold value and a high correlation threshold value, and, based on the correlation factor exceeding the low threshold value and being less than the high correlation threshold value, cancel the ambient light component from the combined optical signal to produce an interrogation signal including the interrogation component.

20 Claims, 2 Drawing Sheets

EXPLOITING CONSTRUCTIVE INTERFERENCE FROM AMBIENT CONDITIONS

BACKGROUND

Optical absorption spectroscopy is a technique to measure the absorption of light due to the interaction of the light with a target object. For example, light may be transmitted and reflected off of the target object. During this process, some of the light is absorbed by the target object while the remaining light is reflected off of the target object and received by an optical receiver. For instance, in photoplethysmography (PPG), transmitted light is reflected off the body of a user and received by a light detector. Different levels of blood oxygenation absorb different wavelengths of light. Therefore, the signal that represents the light that is reflected off of and not absorbed by the target object, in this example, the user's body, may be a function of pulsating arterial blood, non-pulsating arterial blood, venous blood, and other tissues. By analyzing the reflected signal, different parameters may be determined. Continuing the PPG example, the heartrate of the user may be determined by analyzing the resulting reflected signal. Unfortunately, in addition to receiving the reflected signal, ambient light may also be received by the optical receiver. Thus, the received signal may contain a component that is a result of the interrogation by the optical system (i.e., the result of the reflected light) and a second component which is a result of the ambient light. Thus, the system must account for the ambient light when analyzing the received signal.

SUMMARY

The problems noted above are solved in large part by systems and methods for exploiting constructive interference from ambient conditions. In some embodiments, an optical system includes an optical illumination source, an optical receiver, a correlation determination circuit, and an ambient condition control circuit. The optical illumination source is configured to emit a light in the direction of a target object. The optical receiver is configured to receive a combined optical signal that includes an ambient light component combined with an interrogation component. The correlation determination circuit is configured to compare the combined optical signal with an ambient light signal to identify a correlation factor. The ambient condition control circuit is configured to compare the correlation factor to a low correlation threshold value and a high correlation threshold value, and, based on the correlation factor exceeding the low threshold value and being less than the high correlation threshold value, cancel the ambient light component from the combined optical signal to produce an interrogation signal including the interrogation component.

Another illustrative embodiment is a method that may comprise receiving a combined optical signal comprising an ambient light component combined with an interrogation component. The method may also comprise receiving an ambient light signal comprising the ambient light component without the interrogation component. The method may also comprise identifying a correlation factor by comparing the combined optical signal with the ambient light signal. The method may also comprise comparing the correlation factor to a high correlation threshold value. The method may also comprise, based on the correlation factor exceeding the high correlation threshold value, deactivating an optical illumination source.

Yet another illustrative embodiment is an ambient condition control circuit comprising optical illumination power control logic and ambient cancellation control logic. The optical illumination power control logic is configured to, based on a correlation factor exceeding a high correlation threshold value, deactivate an optical illumination source. The correlation factor is identified by comparing a combined optical signal with an ambient light signal. The combined optical signal comprises the ambient light component combined with an interrogation component. The ambient cancellation control logic is configured to, based on the correlation factor exceeding a low correlation threshold value and being less than the high correlation threshold value, cancel an ambient light component from the combined optical signal to produce an interrogation signal.

BRIEF DESCRIPTION OF THE DRAWINGS

For a detailed description of various examples, reference will now be made to the accompanying drawings in which.

NOTATION AND NOMENCLATURE

Figure 1:
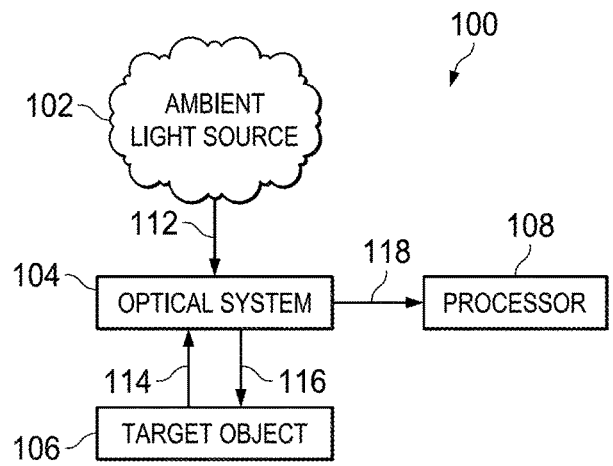
FIG. 1 shows a block diagram of a system for exploiting constructive interference from ambient conditions in accordance with various embodiments.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections. The recitation "based on" is intended to mean "based at least in part on." Therefore, if X is based on Y, X may be based on Y and any number of other factors.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Optical absorption spectroscopy is a technique to measure the absorption of light due to the interaction of the light with a target object. For example, light may be transmitted and reflected off of the target object. During this process, some of the light is absorbed by the target object while the remaining light is reflected off of the target object and received by an optical receiver. In addition to receiving the reflected signal, ambient light may also be received by the optical receiver. Thus, the received signal may contain a component that is a result of the interrogation by the optical system (i.e., the result of the reflected light) and a second component which is a result of the ambient light. Thus, the system must account for the ambient light when analyzing the received signal.

Conventional systems account for the ambient light either mechanically or electrically. Mechanical solutions act to physically block the ambient light from being received by optical receiver. In other words, mechanical solutions act to mechanically decouple ambient light. However, many optical absorption spectroscopy systems are incorporated into small objects, such as a watch to be worn by a user. These mechanical solutions are bulky, uncomfortable, and/or difficult to incorporate into a small object that a user would wish to wear. Therefore, electrical solutions are preferable. Conventional electrical solutions measure the received signal that includes the result of the interrogation (the signal of interest) combined with the ambient light and separately measure just the ambient light. The separately measured ambient light is then subtracted from the combined received signal to produce the interrogation signal (signal of interest) to be further analyzed. However, the act of subtracting the ambient light from the combined signal may increase noise in the resulting signal which is actually worse than the original combined signal. Furthermore, in high ambient conditions, the signal of interest may be present in the separately measured ambient light. In these conditions, subtracting the ambient light from the combined signal may subtract out the signal of interest. Therefore, there is a need to account for ambient light in a way that does not degrade the signal of interest that is to be processed.

In accordance with the disclosed principles, a system may be employed that analyzes both the combined received signal and the separately measured ambient light to determine how correlated these two signals are. If it is determined that the two signals are highly correlated, then the ambient signal itself includes the signal of interest and may be considered the interrogation signal to be processed. In this situation, the optical illuminator utilized to transmit the light may be deactivated as the ambient light signal is utilized. In other words, because the signal of interest is embedded in the ambient signal, the optical illuminator (e.g., an LED illuminator) may be turned off because the ambient light itself provides the same benefit as if the optical illuminator is still activated. This reduces power consumption in the system. However, it if is determined that the two signals are minimally correlated, then the system utilizes the combined received signal as the interrogation signal to be processed. Because applying electrical ambient cancellation adds noise and worsens SNR, ambient cancellation is not applied when the two signals are minimally correlated. Instead, SNR is preserved, and the signal may be post-processed through a digital bandpass filter downstream where the uncorrelated ambient component will be removed. If it is determined that the two signals are not highly correlated and are not minimally correlated (i.e., they are correlated a medium amount), then the system acts to cancel the ambient component of the combined received signal by subtracting the separately measured ambient light from the combined received signal. This leaves only the signal of interest remaining. Because certain components of the ambient signal are similar to components of the signal of interest, the ambient signal is removed from the combined received signal, even at the expense of lowering the SNR, to avoid contamination from the ambient signal.

FIG. 1 shows a block diagram of a system 100 for exploiting constructive interference from ambient conditions in accordance with various embodiments. The system 100 may include an ambient light source 102, an optical system 104, a target object 106, and a processor 108. The ambient light source 102 may be a light source or sources that are of the surrounding area or environment of the optical system 104 and target object 106. In other words, the ambient light source 102 may be any light that may be received by optical system 104 and target object 106 that is not originally generated by the optical system 104. For example, the ambient light source 102 may include sunlight, overhead lighting in a room, light emitted from a television, candlelight, etc. or any combination of sources. The ambient light source 102, thus, provides an ambient light signal 112 that may be received by the optical system 104 directly and/or be received after reflecting off of target object 106.

Optical system 104 is an optical system that is configured to emit a light 116 in the direction of a target object, such as target object 106 and receive a combined optical signal 114 from the target object 106. The optical system 104 may be an optical absorption spectroscopy system. Therefore, light 116 may be transmitted by the optical system 104 and reflected off of the target object 106. During this process, some of the light 116 is absorbed by the target object 106, while the remaining light is reflected off of target object 106 and received by the optical system 104. For example, in a PPG system, the target object 106 may be a human body where blood and other tissues within the body absorb certain wavelengths of light. More specifically, different levels of blood oxygenation absorb different wavelengths of light. Therefore, the signal that represents the light that is reflected off of and not absorbed by the target object 106 (in some embodiments referred to as the interrogation signal) may be a function of pulsating arterial blood, non-pulsating arterial blood, venous blood, and other tissues. The interrogation signal is then received by the optical system 104. However, in addition to the interrogation signal, the optical system 104 may also receive the ambient light signal 112 at the same time. Thus, the optical system 104 receives a combined optical signal 114 that may be composed of two components: the reflected light that is not absorbed by the target object 104 (i.e., the interrogation signal) and the ambient light signal 112.

The optical system 104 may be configured to identify the interrogation signal 118 from the combined optical signal 114. Once the interrogation signal 118 is identified by the optical system 104, the interrogation signal 118 is transmitted to processor 108 for further processing. Processor 108 may be any type of processor and/or microprocessor with an architecture optimized for processing the interrogation signal 118. For example, processor 118 may be a microprocessor configured to perform calculations to determine a heart-rate based on the interrogation signal 118.

Figure 2:
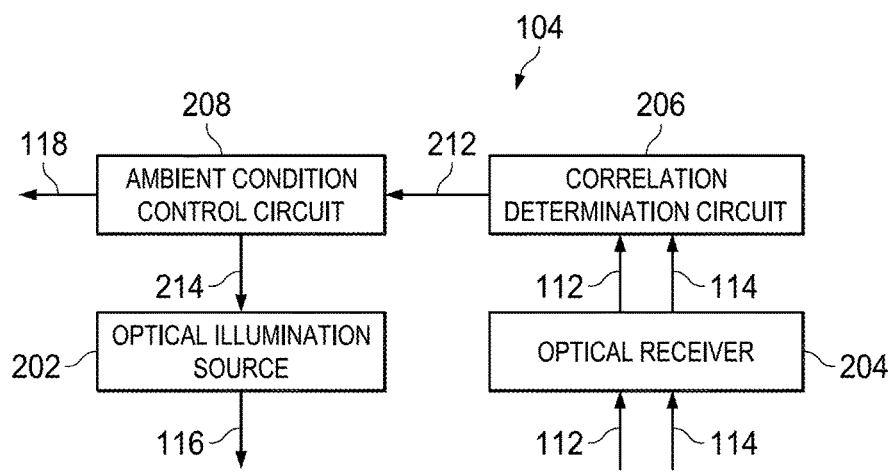
FIG. 2 shows a block diagram of an optical system in accordance with various embodiments.

FIG. 2 shows a block diagram of optical system 104 in accordance with various embodiments. Optical system 104 may include an optical illumination source 202, an optical receiver 204, a correlation determination circuit 206, and an ambient condition control circuit 208. The optical illumination source 202 is configured to emit light 116 in the direction of target object 106. In some embodiments, the optical illumination source 202 is a light emitting diode (LED).

Optical receiver 204 is configured to receive combined optical signal 114 and ambient light signal 112. In some embodiments optical receiver 204 is a photodiode that absorbs photons of light in combined optical signal 114 and/or ambient light signal 112 and converts those photons of light into a current that represents combined optical signal 114 and/or ambient light signal 112. While only a single optical receiver 204 is depicted in FIG. 2, multiple optical receivers may be present. For example, one optical receiver may be configured to receive the combined optical signal 114 while the second optical receiver may be configured to receive the ambient light signal 112. In an embodiment in which a single optical receiver 204 is employed, the optical illumination source 202 may be configured to emit light 116 during a first period of time while deactivating during a second period of time. Thus, the optical receiver 204 receives the combined optical signal 114 during the first period of time while receiving only ambient light signal 112 during the second period of time. Therefore, whether utilizing a single optical receiver 204 or multiple optical receivers, both the combined optical signal 114 and the ambient light signal 112 without the interrogation signal present are received.

The correlation determination circuit 206 may be configured to receive the combined optical signal 114 and the ambient light signal 112 from the optical receiver 204. The correlation determination circuit 206, which may be hardware and/or a microcontroller that implements instructions that cause the processor to compare the combined optical signal 114 and ambient light signal 112 to identify a correlation factor 212. In other words, the correlation determination circuit 206 may act to compare the ambient light signal 112 with the combined optical signal 114, which is composed of an interrogation component that corresponds to the interrogation signal 118 and an ambient light component which corresponds to the ambient light signal 112, to determine the amount of correlation between the signals (i.e., determine how structurally similar are the two signals). The correlation determination circuit 206 then may assign a correlation factor 212 based on the amount of correlation between the combined optical signal 114 and ambient light signal 112. In an embodiment, the more correlated the combined optical signal 114 and ambient light signal 112 are to one another, the greater the correlation factor 212 assigned by the correlation determination circuit 206.

Figure 3:
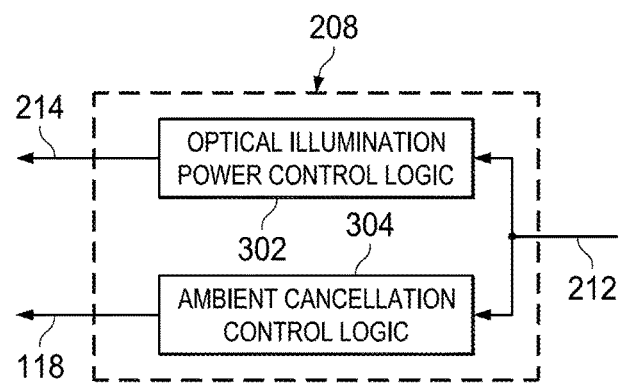
FIG. 3 shows a block diagram of an ambient condition control circuit in accordance with various embodiments.

FIG. 3 shows a block diagram of ambient condition control circuit 208 in accordance with various embodiments. The ambient condition control circuit 208 may include optical illumination power control logic 302 and ambient cancellation control logic 304. Each of the optical illumination power control logic 302 and ambient cancellation control logic 304 may be configured to receive the correlation factor 212 from the correlation determination circuit 206. The optical illumination power control logic 302, which may be hardware and/or a microcontroller that implements instructions that cause the processor to compare the correlation factor 212 to a high correlation threshold value. The high correlation threshold value may be programmable in the optical illumination power control logic 302 and may be set such that any correlation factor that exceeds the high correlation threshold value is considered a high correlation between the combined optical signal 114 and ambient light signal 112. Because the correlation is considered to be high between the combined optical signal 114 and ambient light signal 112 if the correlation factor 212 exceeds the high correlation threshold value, the ambient light signal 112 may act as the interrogation signal 118. In other words, because the combined optical signal 114 and the ambient light signal 112 are structurally similar, the interrogation component of the combined optical signal 114 is found in the ambient light signal 112. Therefore, in response to a determination that the correlation factor exceeds the high threshold correlation value, the optical illumination power control logic 302 may send a deactivation signal 214, as shown in both FIGS. 2 and 3, that acts to deactivate the optical illumination source 202. Therefore, the ambient light signal 112 is the only signal received by the optical system 104 and is transmitted as the interrogation signal 118 to the processor 108. Because the optical illumination source 202 is deactivated, power is saved in the optical system 104 while maintaining the SNR of the interrogation signal 118.

However, if the correlation factor 212 is less than the high correlation threshold value, the optical illumination source 202 remains active and emitting light 116 and/or is activated to emit light 116. Additionally, if the correlation factor 212 is less than the high correlation threshold value, the ambient cancellation control logic 304 may compare the correlation factor 212 with a low correlation threshold value. The low correlation threshold value may be programmable in the ambient cancellation control logic 304 and may be set such that any correlation factor that is less than the low correlation threshold value is considered to have a low and/or minimal correlation between the combined optical signal 114 and the ambient light signal 112. Because the correlation is considered to be low and/or minimal between the combined optical signal 114 and the ambient light signal 112, the ambient cancellation control logic 304 is configured to determine that the combined optical signal 114 is the interrogation signal 118. Because canceling the ambient light component of the combined optical signal 114 creates noise in the resulting signal, combined optical signal 114 may have a better SNR without canceling the ambient component than if the ambient component is canceled. Therefore, if ambient cancellation control logic 304 determines that there is a low correlation between the combined optical signal 114 and the ambient light signal 112, then the combined optical signal 114 provides a better indication as what the true interrogation signal is than the combined optical signal 114 with the ambient light component canceled; therefore, the combined optical signal 114 is determined by the ambient condition control circuit as the interrogation signal 118. The interrogation signal 118 then may be transmitted to processor 108 for further processing. Furthermore, in some embodiments, the combined optical signal 114, acting as the interrogation signal 118 may pass through a bandpass filter in the processor 108 where the uncorrelated ambient light signal 112 may be removed.

If the correlation factor 212 is less than the high correlation threshold value, but exceeds the low correlation threshold value, the correlation factor 212 is considered to have a medium correlation between the combined optical signal 114 and the ambient light signal 112. Because the correlation is considered to be medium between the combined optical signal 114 and the ambient light signal 112, the ambient cancellation control logic 304 is configured to cancel the ambient light component from the combined optical signal 114 leaving only the interrogation component. In other words, because the combined optical signal 114 and the ambient light signal 112 are somewhat structurally similar, the ambient light component of the combined optical signal 114 is canceled from the combined optical signal 114 leaving the interrogation component. While canceling the ambient light component of the combined optical signal 114 creates noise in the resulting signal, because combined optical signal 114 has a medium correlation with the ambient light signal 112, canceling the ambient light component removes a signal that may make it difficult to assess the signal of interest. In other words, because certain components of the ambient signal are similar to components of the signal of interest, the ambient signal is removed from the combined received signal, even at the expense of lowering the SNR, to avoid contamination from the ambient signal. The interrogation component is then identified as the interrogation signal 118. To cancel the ambient light component of the combined optical signal 114, the ambient cancellation control logic 304 may subtract the ambient light signal 112 received by the optical receiver 204 from the combined optical signal 114. Because the ambient light signal 112 corresponds with the ambient component of the combined optical signal 114, subtracting the ambient light signal 112 from the combined optical signal 114 removes the ambient component from the combined optical signal 114 leaving only the interrogation signal 118. The interrogation signal 118 then may be transmitted to processor 108 for further processing.

Each of the high correlation threshold value and the low correlation threshold value may be programmable in the ambient condition control circuit and may be dynamically changed as required by the system 100. For example, the high correlation threshold value may be set at a higher value for some applications, such as a PPG application than for other applications so as to ensure that the resulting interrogation signal 118 is of high enough quality to be processed by processor 108. Similarly, the low correlation threshold value may be set at a higher or lower value for some application than for other applications so as to ensure that the resulting interrogation signal 118 is of high enough quality to be processed by processor 108.

Figure 4:
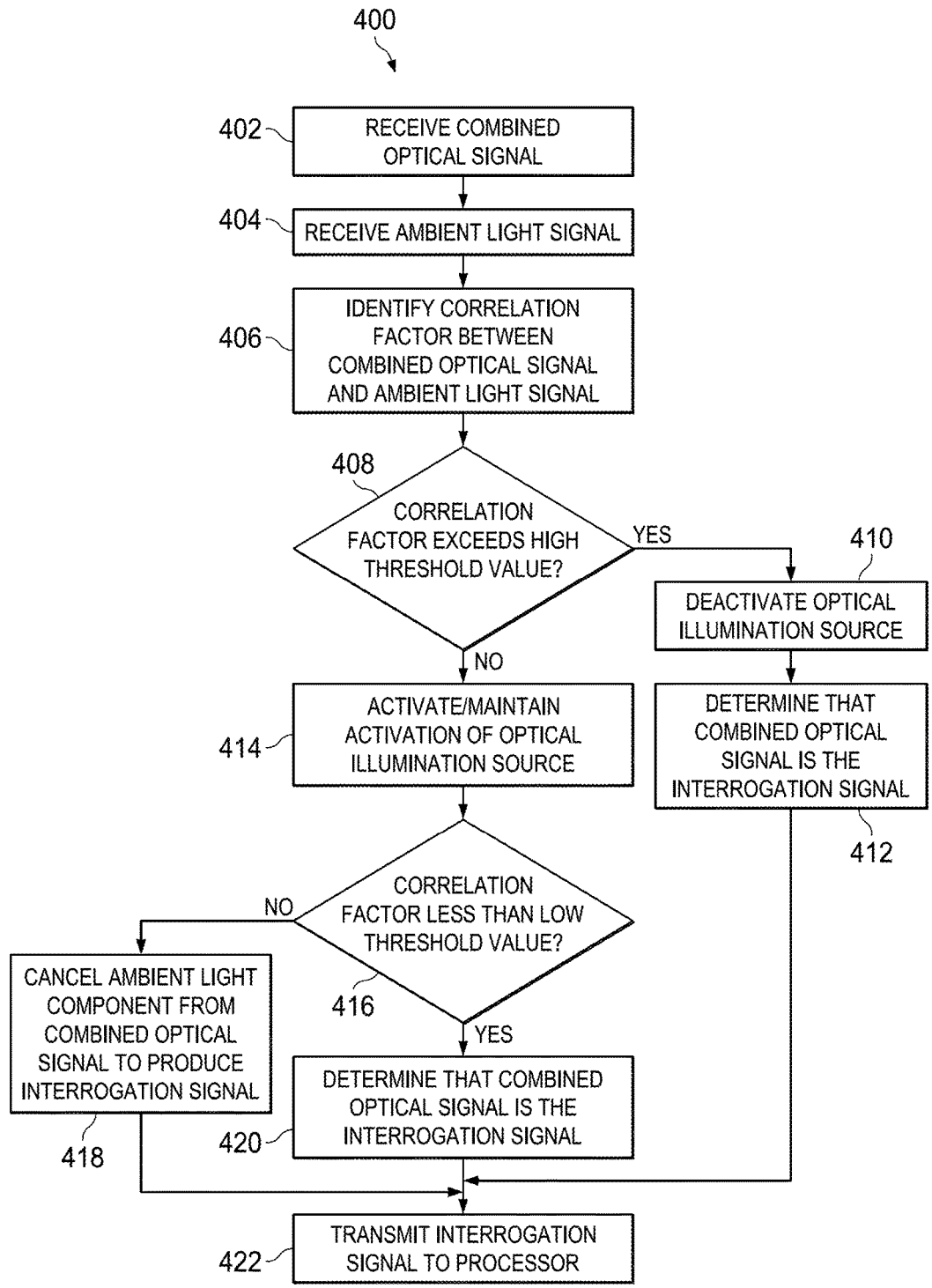
FIG. 4 shows a flow diagram of a method for exploiting constructive interference from ambient conditions in accordance with various embodiments.

FIG. 4 shows a flow diagram of a method 400 for exploiting constructive interference from ambient conditions in accordance with various embodiments. Though depicted sequentially as a matter of convenience, at least some of the actions shown in method 400 can be performed in a different order and/or performed in parallel. Additionally, some embodiments may perform only some of the actions shown or may perform additional actions. In some embodiments, at least some of the operations of the method 400, as well as other operations described herein, can be performed by the optical system 104 implemented by a processor executing instructions stored in a non-transitory computer readable storage medium or a state machine.

The method 400 begins in block 402 with receiving, in some embodiments by optical receiver 204, a combined optical signal, such as combined optical signal 114. The combined optical signal received may include an interrogation component and an ambient light component. In block 404, the method 400 continues with receiving, in some embodiments by optical receiver 204, an ambient light signal, such as ambient light signal 112. The method 400 continues in block 406 with identifying, in some embodiments by correlation determination circuit 206, a correlation factor, such as correlation factor 212, between the combined optical signal and the ambient light signal. The correlation factor may be based on how structurally similar the combined optical signal and the ambient light signal are to one another. In an embodiment, the more structurally similar the combined optical signal is to the ambient light signal, the higher the correlation factor.

In block 408, a determination is made, in some embodiments by optical illumination power control logic 302, whether the correlation factor exceeds a high correlation threshold value. If, in block 408 a determination is made that the correlation factor does exceed the high correlation threshold value, then the method 400 continues in block 410 with deactivating an optical illumination source, such as optical illumination source 202. In block 412, the method 400 continues with determining that the combined optical signal is an interrogation signal, such as interrogation signal 118. Because the optical illumination source is deactivated, the combined optical signal consists solely of the ambient light component. The method 400 continues in block 422 with transmitting the interrogation signal to a processor, such as processor 108 for further processing.

If, in block 408 a determination is made that the correlation factor does not exceed the high correlation threshold value, then the method 400 continues in block 414 with activating/maintaining the activation of the optical illumination source. The method 400 continues in block 416 with determining, in some embodiments by ambient cancellation control logic 304, whether the correlation factor is less than a low correlation threshold value. If in block 416 a determination is made that the correlation factor is not less than the low correlation threshold value, then in block 418, the method 400 continues with canceling the ambient light component from the combined optical signal to produce the interrogation signal. The canceling may comprise subtracting the ambient light signal from the combined optical signal. The method 400 continues in block 422 with transmitting the interrogation signal to a processor, such as processor 108 for further processing.

If, in block 416 a determination is made that the correlation factor is less than the low correlation threshold value, then in block 420, the method 400 continues with determining that the combined optical signal is the interrogation signal. The method 400 then continues in block 422 with transmitting the interrogation signal to a processor, such as processor 108 for further processing.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An optical system, comprising:
    an optical illumination source configured to emit a light in the direction of a target object;
    an optical receiver configured to receive a combined optical signal comprising an ambient light component combined with an interrogation component;
    a correlation determination circuit configured to compare the combined optical signal with an ambient light signal to identify a correlation factor; and
    an ambient condition control circuit configured to compare the correlation factor to a low correlation threshold value and a high correlation threshold value, and, based on the correlation factor exceeding the low threshold value and less than the high correlation threshold value, cancel the ambient light component from the combined optical signal to produce an interrogation signal comprising the interrogation component.

2. The optical system of claim 1, wherein the ambient condition control circuit is further configured to, based on the correlation factor exceeding the high correlation threshold value, deactivate the optical illumination source.

3. The optical system of claim 2, wherein the ambient condition control circuit is further configured to, based on the correlation being less than the low correlation threshold value, determine that the combined optical signal is the interrogation signal.

4. The optical system of claim 3, wherein the ambient condition control circuit is further configured to transmit the interrogation signal to a processor for further processing.

5. The optical system of claim 1, wherein the optical receiver is further configured to receive the combined optical signal during a first time period and to receive the ambient light signal during a second time period.

6. The optical system of claim 1, further comprising a second optical receiver configured to receive the ambient light signal.

7. The optical system of claim 1, wherein the high threshold value and the low threshold value is programmable in the ambient condition control circuit.

8. The optical system of claim 1, wherein the interrogation signal is a photo-plethysmography (PPG) signal.

9. The optical system of claim 1, wherein the optical illumination source is a light emitting diode (LED).

10. A method comprising:
receiving a combined optical signal comprising an ambient light component combined with an interrogation component;
receiving an ambient light signal comprising the ambient light component without the interrogation component;
identifying a correlation factor by comparing the combined optical signal with the ambient light signal;
comparing the correlation factor to a high correlation threshold value; and
based on the correlation factor exceeding the high correlation threshold value, deactivating an optical illumination source.

11. The method of claim 10, further comprising:
comparing the correlation factor to a low correlation threshold value; and
based on the correlation factor exceeding the low correlation threshold value and being less than the high correlation threshold value, canceling the ambient light component from the combined optical signal to produce an interrogation signal comprising the interrogation component.

12. The method of claim 11, wherein the canceling the ambient light component comprises subtracting the ambient light component from the combined optical signal.

13. The method of claim 10, further comprising:
comparing the correlation factor to a low correlation threshold value; and
based on the correlation factor being less than the low correlation threshold value, determining that the combined optical signal is an interrogation signal comprising the interrogation component.

14. The method of claim 10, further comprising:
comparing the correlation factor to a low correlation threshold value;
based on the correlation factor exceeding the low correlation threshold value and being less than the low correlation threshold value, canceling the ambient light component from the combined optical signal to produce an interrogation signal comprising the interrogation component; and
based on the correlation factor being less than the low correlation threshold value, determining that the combined optical signal is an interrogation signal comprising the interrogation component.

15. The method of claim 14, further comprising transmitting the interrogation component to a processor.

16. An ambient condition control circuit, comprising:
optical illumination power control logic configured to, based on a correlation factor exceeding a high correlation threshold value, deactivate an optical illumination source, the correlation factor identified by comparing a combined optical signal with an ambient light signal; and
ambient cancellation control logic configured to, based on the correlation factor exceeding a low correlation threshold value and being less than the high correlation threshold value, cancel an ambient light component from the combined optical signal to produce an interrogation signal;
wherein the combined optical signal comprises the ambient light component combined with an interrogation component.

17. The ambient condition control circuit of claim 16, wherein the ambient cancellation control logic is further configured to, based on the correlation factor being less than the low correlation threshold value, determine that the combined optical signal is the interrogation signal.

18. The ambient condition control circuit of claim 16, wherein the ambient cancellation control logic is configured to cancel the ambient light component by subtracting the ambient light component from the combined optical signal.

19. The ambient condition control circuit of claim 16, wherein the optical illumination power control logic is further configured to, based on the correlation factor being less than the high correlation threshold value, activate the optical illumination source.

20. The ambient condition control circuit of claim 16, wherein the interrogation signal is a photo-plethysmography (PPG) signal.

* * * * *